(12) United States Patent
Tagle

(10) Patent No.: US 9,629,477 B2
(45) Date of Patent: *Apr. 25, 2017

(54) HANDS-FREE SHOULDER CARRIER FOR CHILDREN

(71) Applicant: Reinold Tagle, Encinitas, CA (US)

(72) Inventor: Reinold Tagle, Encinitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/817,157

(22) Filed: Aug. 3, 2015

(65) Prior Publication Data

US 2015/0335171 A1 Nov. 26, 2015

Related U.S. Application Data

(63) Continuation-in-part of application No. 13/945,692, filed on Jul. 18, 2013, which is a continuation-in-part of application No. 13/691,095, filed on Nov. 30, 2012, now Pat. No. 9,095,227, and a continuation-in-part of application No. 29/457,460, filed on Jun. 10, 2013, now Pat. No. Des. 725,375.

(60) Provisional application No. 61/673,083, filed on Jul. 18, 2012.

(51) Int. Cl.
| | |
|---|---|
| *A61G 1/00* | (2006.01) |
| *A47D 13/02* | (2006.01) |
| *A47D 15/00* | (2006.01) |
| *A47D 1/10* | (2006.01) |
| *G01N 5/04* | (2006.01) |
| *G01N 30/72* | (2006.01) |

(52) U.S. Cl.
CPC .............. *A47D 13/025* (2013.01); *A47D 1/10* (2013.01); *A47D 15/006* (2013.01); *G01N 5/04* (2013.01); *G01N 30/7206* (2013.01)

(58) Field of Classification Search
CPC ....... A47D 13/025; A47D 15/006; A47D 1/10
USPC ................................. 224/160, 161, 159, 158
See application file for complete search history.

(56) References Cited

U.S. PATENT DOCUMENTS

| | | | | |
|---|---|---|---|---|
| 3,698,608 | A * | 10/1972 | Entwistle | A47D 13/025 224/159 |
| 3,968,910 | A * | 7/1976 | Dye | A47D 13/025 224/161 |
| 4,416,403 | A * | 11/1983 | Johnson | A47D 13/025 224/159 |
| 4,484,700 | A * | 11/1984 | Bush | A47D 13/025 224/159 |
| 4,746,044 | A * | 5/1988 | Arvizu | A47D 13/025 224/155 |
| 5,437,402 | A * | 8/1995 | Ring | A47D 13/025 128/882 |
| 6,098,856 | A * | 8/2000 | Reilly | A47D 13/025 224/159 |

(Continued)

*Primary Examiner* — Justin Larson
*Assistant Examiner* — Lester L Vanterpool
(74) *Attorney, Agent, or Firm* — Donn K. Harms

(57) ABSTRACT

A child carrier and support apparatus for securing a child in a seated position atop a wearer's shoulders is provided which is adapted to engage with a conventional backpack or strapped carrier. The device features a pair of cuffs engageable with the shoulder straps to removably encircle the ankles of the seated child and a sternum strap engaged between the cuffs to limit the distance of spacing of the shoulder straps. A U-shaped seat has two straps engageable to the two cuffs to hold the seat in operative positioning on the shoulders of the wearer.

8 Claims, 9 Drawing Sheets

(56) References Cited

U.S. PATENT DOCUMENTS

| | | | | |
|---|---|---|---|---|
| 6,241,136 B1* | 6/2001 | Harriss | ................ | A47D 13/025 |
| | | | | 128/882 |
| 8,474,667 B2* | 7/2013 | Schwartz | ............. | A47D 13/086 |
| | | | | 224/159 |
| D698,541 S * | 2/2014 | Schulte, II | ..................... | D3/213 |
| 2002/0179654 A1* | 12/2002 | Pripps | .................. | A47D 13/025 |
| | | | | 224/161 |
| 2009/0200346 A1* | 8/2009 | Long | .................... | A47D 13/025 |
| | | | | 224/158 |
| 2010/0084445 A1* | 4/2010 | Schwartz | ............. | A47D 13/086 |
| | | | | 224/159 |
| 2012/0018467 A1* | 1/2012 | Chiappini | ............ | A47D 13/025 |
| | | | | 224/158 |

* cited by examiner

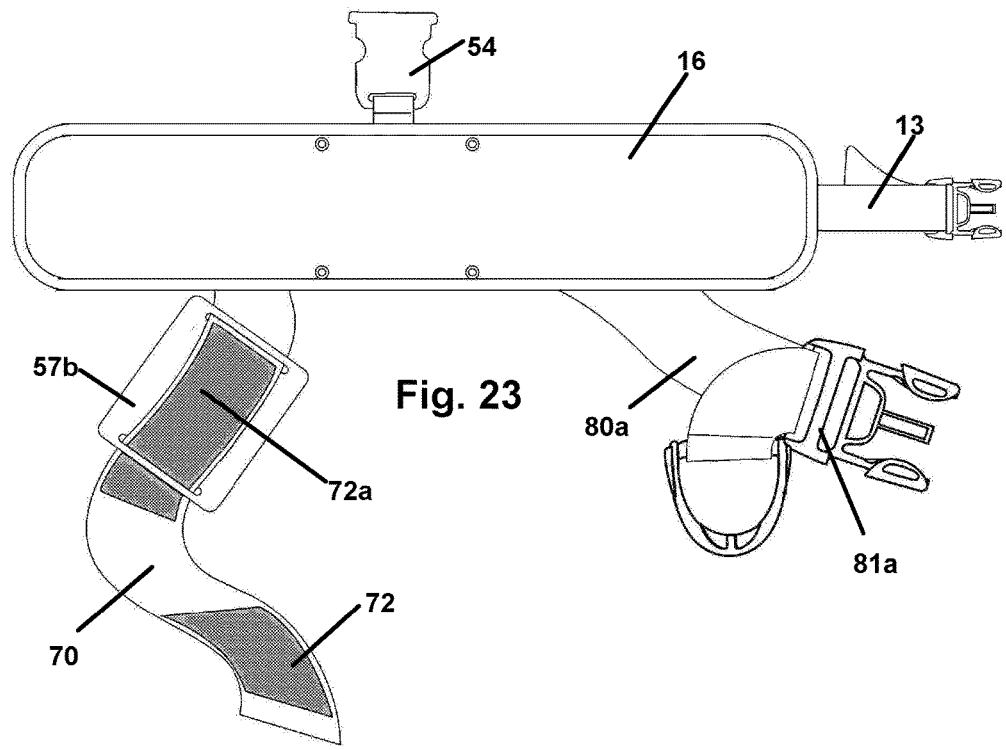
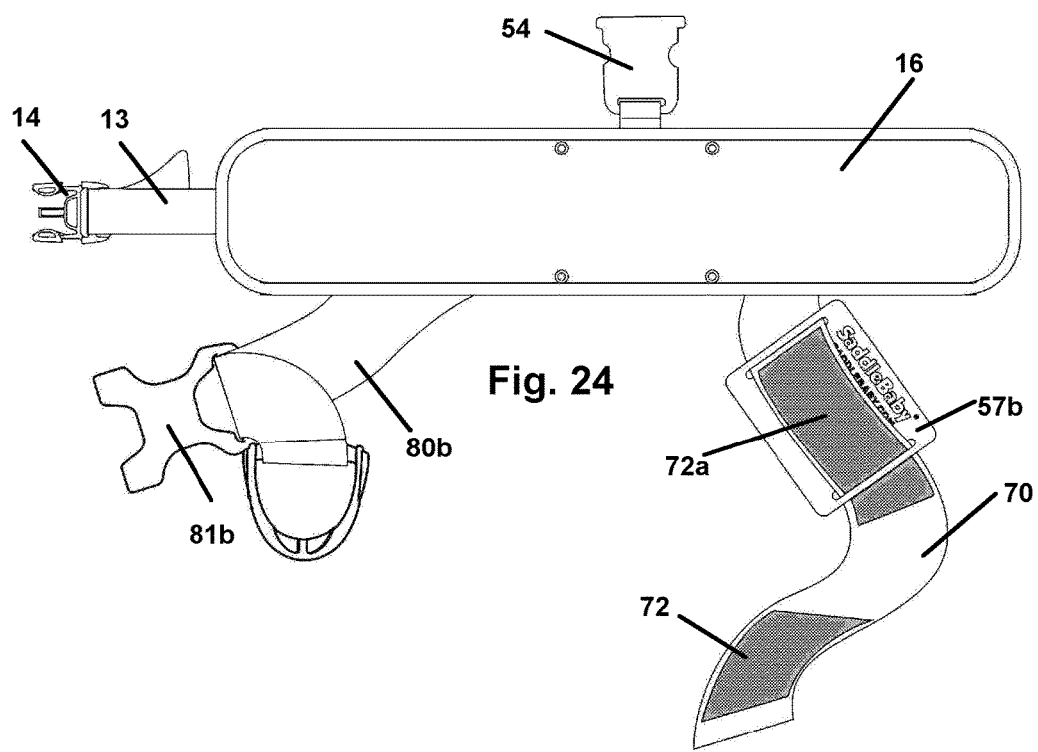

HANDS-FREE SHOULDER CARRIER FOR CHILDREN

This application is a continuation in part application from Ser. No. 13/945,652 filed on Jul. 8, 2013 which claimed priority to U.S. patent application Ser. No. 13/691,095 filed on Nov. 30, 2012 and U.S. Design patent application Ser. No. 29/457460 filed on Jun. 10, 2013 and which claimed priority to U.S. Provisional Patent Application Ser. No. 61/673,083 filed on Jul. 18, 2012, and, all of the aforementioned applications are respectively incorporated herein in their entirety, by this reference thereto.

BACKGROUND OF THE INVENTION

1. Field of the Invention

The present invention relates to the carrying of children by adults and larger persons than the carried child. More particularly the invention relates to a device configured to provide and interface between the carrying person and the carried child and to provide hands-free but very secure seating to a child occupying a seat atop the shoulders of an adult. The device provides a safer and more comfortable experience to both child and the carrying-adult through the provision of strategically positioned and configured seat padding and retaining straps.

2. Prior Art

The carrying of children, especially toddlers, upon the shoulders of an adult or older sibling, has been a favorite mode of transport for the carried child throughout history. For the child, it is a chance to see the world from an entirely different perspective than walking, as well as a chance to rest small legs which must work twice as hard to keep up with walking adults.

For the adult carrying the child, it is a mode of carrying the child to keep the child safe and above potential harm which might lurk on the ground. For example, it is also very helpful when walking in crowded places where the child may get stepped on or separated from the adult, like busy transportation terminals, amusement parks, etc. It is also an easy manner to take control of the child's movement, without having to order the child, since most children willingly and enthusiastically jump at the chance to ride above the crowd on the parent's shoulders.

However, for child and carrying-adult alike, the duration the child occupies the elevated position riding upon the shoulders, can be inversely proportional to the pleasurable nature of the ride to both. For the carrying adult, the weight of the child upon their shoulders, and need to use their hands to control and balance the child, can tend to cause muscle exertion and strain. Additionally, the compressive nature of the weight of the child bearing against the adults shoulder and neck muscles and bones, and the continual force of the child pulling on their head or neck to maintain themselves upright, can be a source of pain and discomfort significant enough to cause a discontinuance of the ride.

For the child, a bony adult can make for a rough ride. Further, for smaller children who may lack the muscle strength and coordination to hold their backs erect and the legs properly positioned over the shoulder, the ride can be uncomfortable, unbalanced, and even scary.

This fear may not only be a problem with the child. The carrying adult of small children may be continually in fear of the child losing their grip or balance and sliding off or falling backward out of their line of sight. Or, the non carrying adult walking with them may have the same fear since they have no feedback as to the child's dexterity and sense of balance. While carrying a child on ones shoulders has been practiced throughout history, concern of the carrier, non carrier, and child, as well as the duration of the ride, can cause the experience to be less than desirable.

Conventionally, carrying a child on the shoulders has often required the holding of the child's ankles by the carrier's hands, wherein the child is stabilized and generally prevented from falling backwards. However, a slip of the hands by the adult carrier while the child is leaning backward can have serious results.

Moderately complicated framed carrying devices have also developed and been employed, wherein the child is placed in the framed carrying device and the carrying apparatus is fitted on the carrier's back or shoulders. An example can be found in U.S. Pat. Nos. 4,746,044; 6,098,856; and 6,561,394.

However such conventional framed carrying devices are often heavy, cumbersome, and not easily portable. Further these and similar devices unnecessarily fully support the back and upper body of the child, when it is conventionally only required to secure the child at their ankles. In addition, these devices which fully support the child's back are intended for carrying young children or infants who may not have the muscle strength or coordination to support themselves in an upright seated posture, however since they are substantially rigid, they can become a proverbial pain in the neck for the adult or carrying person.

As such there is a continuing and unmet need for a child carrier device employable for carrying a child atop the shoulders of an adult or larger child, which eliminates the need for a bulky, rigid, heavy and cumbersome frame. Such a device should still provides a secure and comfortable ride for the adult and child. Such a device should employ flexible members such as webbing type straps to provide a flexible yet sturdy framework which can be engaged about the users upper body and shoulders.

Further, such a device should employ means to secure the ankles of the child when in the carrying position atop the users shoulders to eliminate the need to hold the ankles with upraised arms. Additionally, such a device should provide a seat configuration and child adult interface, to further aid in wider distribution the weight load about the users for improved comfort and ease of use. Further, in an as-used position, such a device should be hands free for the carrying adult, while extremely secure for the carried child thereby elevating anguish on the part of both. Still further, it is preferred that such a device should be employable with young children who are developed enough to maintain themselves in an upright seated posture without the aid of a full back rest.

Still further, such a device should be provided in both a full system of flexible members for carrier-engagement as well as a kit to retrofit the shoulder harnesses already owned and used by carrying adults such as backpacks.

The forgoing examples of related art and limitation related therewith are intended to be illustrative and not exclusive, and they do not imply any limitations on the invention described and claimed herein. Various limitations of the related art will become apparent to those skilled in the art upon a reading and understanding of the specification below and the accompanying drawings.

SUMMARY OF THE INVENTION

The device herein disclosed and described provides a solution to the shortcomings in prior art and achieves the above noted goals through the provision of child carrier and securement device for providing secure and comfortable seating to a child occupying a seat atop the shoulders of an adult.

In accordance with one preferred mode, the carrier and securement device are comprised from a flexible strap member configured for a secured as-used positioning in an engagement around the upper chest or bust of the adult user. The flexible member forming the chest strap may be formed from conventional materials such as fabric or fabric webbing however can be formed of any material suitable for the purposes set forth in this disclosure.

Further, in the mode where the flexible members are provided, the chest strap may be padded or otherwise cushioned to provide additional comfort to the adult user. To accommodate various chest sizes, the straps forming the flexible members' engagement, may be length-adjustable and employ fasteners to allow the user to easily engage and disengage the device from the as used position. Types of fasteners may include plastic fasteners, snap fit, buckle, hook and loop fasteners, and others suitable fasteners known in the art such as any suitable cooperative fastener from the GRAINGER catalog.

In another preferred mode of the device, the chest strap is adjustable via a tightening or loosening of a distal end of the strap relative the buckle or other fastener. This adjustability can be compared to that employed in conventional backpack shoulder straps, and the like. However, additional utility is provided in that the distal end of adjustable strap may be form in a substantially T-shaped cross section, similar to that found in M.O.L.L.E (Modular Lightweight Load-carrying Equipment) straps. In this mode, after securing the buckle or other fastener, the distal end of the strap can be communicated back over the buckle and secured to the opposite side of the chest strap and provide a redundant safety securement of the chest strap around the user's chest.

In yet another preferred mode, the device features a pillow interface which is adapted for secure engagement with the seat of a seated child on the shoulders of a carrying person or adult, in the as-used position of the device. This pillow features an upper surface contoured to provide a recess for the posterior of the seated child, which communicates with parallel leg recesses. Channels are formed in the pillow for communication of the flexible members therethrough to thereby hold the pillow in a position behind the neck of the carrying person. The pillow may be employed with any mode of the flexible members or strap-engageable ankle securement components or members.

The device additionally includes ankle securement members which as noted herein, may be provided for use in combination with provided flexible securement members, or, may be removably engaged to the user's existing strap or flexible member device adapted for shoulder engagement, such as a backpack. These ankle securement members provide a means to secure the ankles and legs of the carried child abutting the chest of the user when the device is in the as-used mode where the device is engaged about the chest or upper torso of the adult user, or child-carrying person, and with the child in a conventional seated position atop the users shoulders. These ankle securement members are configured to removably engaged about the ankles or legs of the child's feet using cooperative fasteners on opposing distal ends of each ankle securement member. So engaged around the lower leg of the child adjacent the foot, this will eliminate the requirement for the user or carrier to hold the child's ankles with their hands and with their arms elevated, as is conventionally done to stabilize and prevent the child from falling backwards. So engaged to the legs of the child, and also engaged to a flexible member provided, or of another device such as a backpack, the ankle securement member will provide comparable if not greater leg securement than that of an adult user gripping by hand. Thus, the device in the as-used position, provides a 'hands free' securement device for a child positioned atop the users shoulders.

In accordance with another preferred mode of the device, a seating component configuration is provided on the back of the device, and therefor on the back of the users when in the as used mode. The seating component is engaged to the flexible members in a position opposite the ankle securement members. In this mode the seating component may be formed from a flexible material such as textile fabric, or molded material, or the like. The seating component is preferably contoured to provide an ergonomic seating arrangement for the child, like a type of saddle.

Those skilled in the art will recognize various ergonomic seating configurations, shapes, and contours may be formed and are suitable for the intended purpose, and all such seating configurations providing a recessed positioning of a child seated behind the head of a carrying person, are anticipated and considered part of this disclosure. The saddle type configuration of the seating component will provide comfortable seating for the child without the need to provide a full back support, such that the child uses their back muscles to maintain an upright seating which also provides exercise and eliminates the possibility that the back support can rub or irritate on the child. However, in other modes if desired, the seating component could additionally be provided with a full back support extending vertically from the rear edge of the pillow or seat.

The seating component preferably engages with a member engaged to, or to, shoulder securement straps, which extend from the front of the chest strap and ankle securement members to an operative engagement with the seat. The flexible members or straps may be padded or otherwise cushioned on one or both sides to provide comfort for both the carrying adult and seated child.

The shoulder straps, if provided with the ankle securement members, may be length-adjustable. In one preferred mode, the exposed surface of the shoulder straps have a surface which is concaved. This concave surface area can be provided by formed padding which is concaved and provides a means for registered positioning and padded engagement of the seated child's legs hanging over the adult's chest. This recessed and registered leg positioning provides comfort to the seated child over prolonged seating since their legs will not be rested against a raised or otherwise protruding surface of the strap. Further, the child's legs are maintained in an aligned position with the ankle securement members without having to use the leg muscles.

The disclosed seating component is configured in a type of backpack configuration with the provided straps, or when employed with the user device having straps, such that the weight of the child positioned in the seat, is advantageously communicated to the shoulder straps and chest strap, and away from the users neck. Therefor the device provides a means to communicate the load of the weight of the carried child, to the entire upper body and eliminate the stress and strain conventionally imparted on the user neck and back when carrying a child on their shoulders.

In accordance with at least one preferred mode of the invention, the ankle securement members are provided by elongated flexible straps formed to substantially U-shaped members having hooked distal ends or other cooperative fasteners thereon. The members are preferably formed from a flexible plastic or other suitable material. In use, the child's ankles or other leg portion are engageable into the U-shaped members through a slight or moderate inward flexure of the distal ends. Securement is preferred in the manner of the hooked distal ends which tend to resist an outward flexure therefor resisting disengagement of the child's ankles from the U-shaped members. However, disengagement can be accomplished by the adult user flexing the hooked ends outward, or by other cooperative fasteners which resist unaided detachment.

Further, in yet another preferred mode, the U-shaped members, or flexible ankle securement members, may be rotatably engaged to the flexible shoulder or chest straps. This means for rotational engagement allows the child to maintain a natural leg angular position which may be slightly or moderately angled relative the vertical. Rotatably engagement can be accomplished by a swivel fastener, rotatable engagement with a rivet, or other suitable means for rotational engagement of the ankle securement member to the strap.

Still further, in yet another preferred mode, the ankle securement members can be provided straps having releasable cooperative fasteners. The straps may be padded or otherwise cushioned to provide additional comfort to the child. The releasable fasteners can be any suitable fastener such as buckle, hook and loop fasteners, or the like. This mode may be employed where the device is provided with the flexible members for chest and shoulder securement, or, where the ankle securement members are provided for engagement to the user's existing strapped device such as a backpack.

The device in another mode also provides with cuffs which are securable to any vertically disposed strap in a fixed positioning. Each cuff in this mode will engage with the other as well as with one strap depending from a shoulder-positioned pillow or pad.

In all modes of the device, the ankle securement members may be engaged to one or both of the chest strap and shoulder straps or to components communicating therewith. So engaged, the ankle securement members must maintain the lower leg of the child seated on the user's shoulders, adjacent to the front of the user's body.

With respect to the above description, before explaining at least one preferred embodiment of the herein disclosed invention in detail, it is to be understood that the invention is not limited in its application to the details of construction and to the arrangement of the components in the following description or illustrated in the drawings. The invention herein described is capable of other embodiments and of being practiced and carried out in various ways which will be obvious to those skilled in the art. Also, it is to be understood that the phraseology and terminology employed herein are for the purpose of description and should not be regarded as limiting.

As such, those skilled in the art will appreciate that the conception upon which this disclosure is based may readily be utilized as a basis for designing of other structures, methods and systems for carrying out the several purposes of the present disclosed device. It is important, therefore, that the claims be regarded as including such equivalent construction and methodology insofar as they do not depart from the spirit and scope of the present invention.

As used in the claims to describe the various inventive aspects and embodiments, "comprising" means including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

It is an object of the present invention provide a comfortable and hands-free seating of a child atop an adult users shoulder.

It is another object to transfer the weight of the child atop the users shoulder away from the users head and neck.

It is another object of the invention to provide releasable ankle securement members for securing a child's lower legs and feet abutting or adjacent to the users chest in the as-used mode.

It is a further object of the invention to be employable with a provided flexible member harness, or to be configured to engage existing strapped devices for use in combination therewith.

It is yet a further object of the invention, to provide a padded interface between the recess occupied by the posterior of the child, and the user's neck and shoulders.

It is yet another object of this invention to provide the device with cuffs configured to engage any strapped carrier such as a backpack with once engaged will also secure to each other as well as anchor a shoulder-positioned pillow or pad to maintain the straps adjacent and the pillow or pad securely positioned.

These and other objects features, and advantages of the present invention, as well as the advantages thereof over existing prior art, which will become apparent from the description to follow, are accomplished by the improvements described in this specification and hereinafter described in the following detailed description which fully discloses the invention, but should not be considered as placing limitations thereon.

BRIEF DESCRIPTION OF DRAWING FIGURES

The accompanying drawings, which are incorporated herein and form a part of the specification, illustrate some, but not the only or exclusive, examples of embodiments and/or features. It is intended that the embodiments and figures disclosed herein are to be considered illustrative of the invention herein, rather than limiting. In the drawings:

FIG. 5b shows a front view of the mode of the ankle member of FIG. 5a.

FIG. 6b shows a front view of the mode of the ankle member of FIG. 6a.

FIG. 23 shows a front view of the cuff of FIG. 21 and additionally depicts the hook and loop fabric positioned for holding the clamp halves engaged with a strap.

FIG. 24 depicts a front view of cuff of the cuff of FIG. 22 also showing hook and loop fabric as in FIG. 23.

DETAILED DESCRIPTION OF THE PREFERRED EMBODIMENTS OF THE INVENTION

Figure 1:
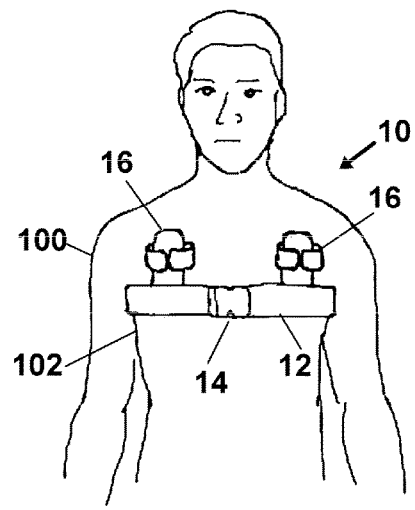
FIG. 1 shows a front view of a first particularly preferred mode of the securement device in the as used position on a user.
Figure 2:
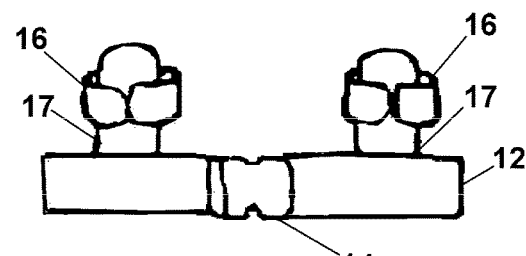
FIG. 2 shows a front view of the device of FIG. 1.

In this description, the directional prepositions of up, upwardly, down, downwardly, front, back, top, upper, bottom, lower, left, right and other such terms refer to the device as it is oriented and appears in the drawings and are used for convenience only; they are not intended to be limiting or to imply that the device has to be used or positioned in any particular orientation.

Figure 3:
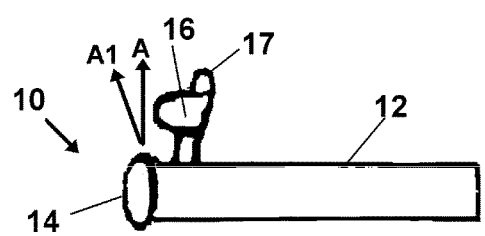
FIG. 3 shows a side view of the device if FIG. 1.
Figure 4:
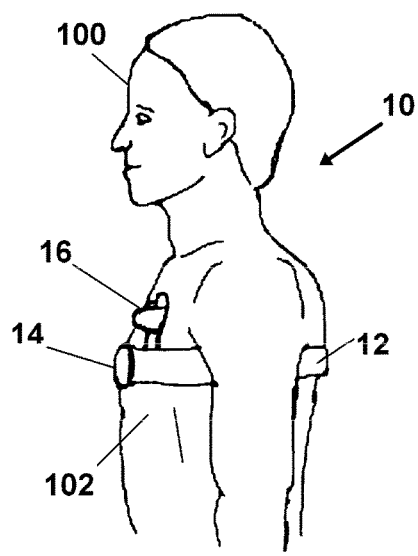
FIG. 4 shows a side view of the device of FIG. 1 in the as used position on a user.

Now referring to drawings in FIGS. 1-24, wherein similar components are identified by like reference numerals, there is seen in FIG. 1, FIG. 2, FIG. 3, and FIG. 4, respective views of a first particularly preferred mode of the child carrier and securement device 10. As shown in FIGS. 1 and 4 the device 10 is situated in the as-used mode engaged around the bust 102 of a user 100 who would be an adult or an adolescent large enough to comfortably support a child.

The device 10 includes a first flexible member defining the chest strap 12 which may be length adjustable, and includes a cooperatively engaging securing fastener 14 as a means for engagement of the first end of the chest strap 12 to the second end thereof. The fastener 14 may be a two-piece complimentary metal or plastic fastener where one component cooperatively engages the other, or any other suitable fastener known in the art for the secure engagement of distal ends of a strap to each other. Such means for strap fastening can include snap fits, two-piece mating snaps or clips, buckles, hooks and other strap fastening means adapted to provide removable, adjustable engagement of one end of the strap to the other. The various components of the device disclosed herein can be formed of conventional materials such as fabric, webbing, plastic, however can be formed of any material suitable for the purposes set forth in this disclosure.

The device 10 additionally includes flexible leg or ankle securement members 16, engaged with a flexible mounting member 17 extending from a first end engagement with the chest strap 12. The securement members 16 are engaged with a mounting member 17 engaged to the chest strap 12 to respective positions adapted to comfortably engage the ankles or portions of the legs adjacent to the ankles of a siting child, in a proper biomechanical posture and provide a means for encircled engagement thereof which is connected to the chest strap 12.

In an as-used engagement of the device 10, with the chest strap 12 sized for an encircled engagement with the torso of a wearer between the waist and shoulders, a child seated atop the users shoulders, extends their legs over the users chest, which situates the child's feet, a distance below the top edge of the user's shoulder. The securement members 16 are configured to engage around a portion of each of the legs, at or adjacent to the ankles adjacent the child's feet, to eliminate the need for the user to grab the child's leg adjacent to or at the angles by hand to provide securement. So engaged, the securement members 16 hold the child's legs against the wearer's torso and provide a means for preventing a rearward fall of the child, especially when the child removes his hands from the wearer's person.

Additionally, because the mounting member 17 is mounted at only a first end to the chest strap 12, whether formed of flexible or resilient material, it can act as a pivoting engagement to allow an angled positioning (A1 of FIG. 3) of the securement members 16, relative to the relatively perpendicular line (A of FIG. 3) which would be the case if the mounting members 17 were mounted on two ends, directly to the front of the chest strap 12. Since the mode of the device of FIGS. 1-6 would frequently be employed for an older child who has sufficient balance and coordination to keep themselves more secure atop the shoulders of the wearer, the pivoting mount providing the angled positioning of the mounting members 17 provides a means to align the axis of the internal cavity of the strap members 16 with the incoming angled lower leg of the child.

Thus the pivoting mounting members 17 accommodate kids with longer legs who may have to angle their lower leg, below the knee to properly position their legs adjacent the ankles within the securement members 16. The angled positioning represented by line A1 of FIG. 3, shows the angle the mounting member 17 will pivot to assume to provide an axial pathway within the strap members 17 for such a child with long legs.

Because this mode of the device 10, provides a much more comfortable fit to the child-user, it will encourage use and will prevent chaffing and skin irritation the strap members 16 might cause on a child if not pivotally engaged by the hinge-like angling of the mounting member 17.

Figure 5B:
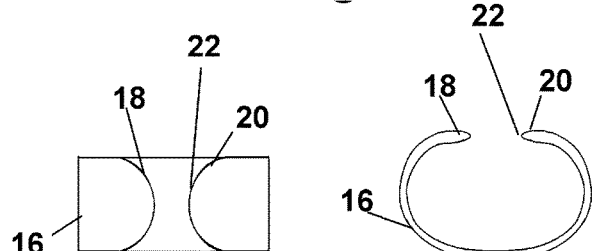
Figure 5A:
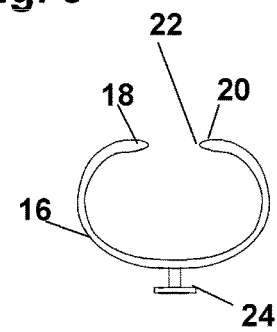
FIG. 5a depicts a top view of a first particularly preferred mode of the ankle engagement members.

Still further, in a preferred mode of the securement members 16 employed with device 10 shown in FIG. 5a and FIG. 5b, the securement members 16 for the legs adjacent the ankles, which are secured to a mounting member 17 as in FIGS. 1-4, or other mounts as in FIGS. 7-13, are formed by substantially U-shaped individual securement members 16. The opposing securement members 16 as shown, employ means of engagement such as an arc or hooked distal ends 18, 20, forming a gap 22 extending therebetween. The hooked distal ends are formed by an arced section at each distal end, which sections of the distal edge of each distal end facing toward the front of the torso or body of the wearer slightly.

In this mode, the ankle or leg securement members 16 are preferably formed from a flexible member made of a polymer or plastic such as polypropylene, polyethylene, nylon, or other suitable material. In use, the child's ankles or adjacent leg portion are positionable through a gap 22 narrower than the width of the child or rider's leg, only by imparting force to the leg to push it through the narrower gap 22 between the distal end 18, 20, or by a spreading of the strap members 16 by the wearer. The leg moving in the gap in a direction toward the wearer, can more easily can separate the two distal ends and enlarge the gap 22 to the second or larger size to slip therethrough.

However, when the rider or child's leg is encircled by the two curved strap members 16, a force from the rider's leg in a direction away from the wearer's torso, in turn communicates leg force to both distal edges at the terminating distal ends the strap members 16 since the gap in the first position, is smaller than their leg width. The contact of their leg with the surfaces of the distal edges or ends at the ends of the hooked portions, causes a slight flexure of the hooked portion of the distal ends 18, 20, but in an inline direction away from the leg force contacting it. This contact makes it harder for the leg of the rider to separate the opposing members 16 and slide out of the passage or encircled engagement between them.

However, an outward flexure of the central portions of both members 16, in the area between their engagement to the mount, and the hooked portion distal ends, can be accomplished by a biasing of the two members in opposite directions by the hands of the wearer, or with extra force by the leg of the rider. The resulting flexure of the distal ends 18 and 20, and for larger legs the central area of the members 16, provides a means for increasing the size of the gap 22, to accommodate the child's leg area adjacent to their ankle, during ingress to the area surrounded by the interior surface of both members 16.

The flexible material forming the U-shaped members 16 is preferably resilient but elastic in nature such as molded polyethylene or polypropylene, or other resilient but flexible under force materials. As a consequence, the biasing effect of the material to return to its original configuration, will then act to restore the members 16 to their originally formed relative positions, wherein the gap 22 is narrower than the width of the child rider's leg at or near the ankle such as from 0.5 inches to 1.5 inches.

Figure 6A:
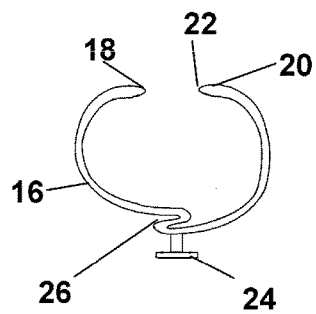
FIG. 6a depicts a top view of another particularly preferred mode of the ankle engagement members having a flexure portion.

Means for maintaining the legs secure from accidental disengagement and within the circular or oval area between the members 16, is provided by the hooked configuration with the distal ends 18 and 20 curving back toward the central portion of the respective body of the members 16 as in FIGS. 5a and 6a. Curved even so slightly to thereby position the distal tips of the distal ends 18 and 20 as the first contact point with the leg of a rider, the distal ends 18, 20 tend to resist the force in a direction away from the wearer's body, required for an outward flexure which would increase the gap 22 size.

Consequently, curving the distal ends 18 and 20 such that the distal tips are the first contact point during disengagement of a leg from the members 16, provides a means to prevent accidental disengagement of the child's ankles from the U-shaped members. In cases where the child can't lean forward and pull the members 16 in opposite directions to increase the gap, leg disengagement can be accomplished through the aid of an adult user who will impart force to pull apart the members 16 and/or hooked ends 18, 20, in opposite directions, to thereby temporarily increase the size of the gap 22 to one larger than the diameter of the child's leg.

In another preferred mode of the ankle members 16, providing additional comfort to the rider and wearer alike, which can be employed in all modes of the device herein, the ankle members 16, are rotatably engaged to the device 10 such as the mount 17 or the chest strap 12 where so configured. The ability to rotate the members 16 surrounding the child's leg during engagement therein, provides a means for the child to comfortably maintain a more natural biomechanical leg position. When sitting on the shoulders of the wearer, the child's legs may be slightly or moderately angled vertically, in radial directions around the center of each pair of members 16. This occurs when the legs of the rider or child are angled outward around the head of the wearer such that their knees are spaced from each other a distance wider than the spacing of the pairs of mount.

The rotatable or pivoting engagement of each pair of members 16, at their mounting point to the device 10, allows them to pivot and radially position the axial passage running through each pair of members 16, to match the line running through a sitting child's leg from their knee. A secure rotating or pivoting engagement can be accomplished by a swivel fastener 24, or similar rotatable rivet and aperture engagement, a fastener having an axle and bearing, or other suitable means for rotatable engagement.

Figure 6B:
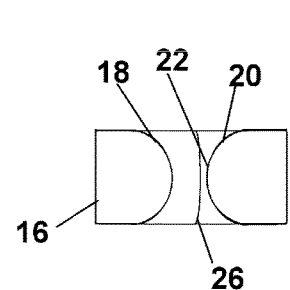
Figure 7:
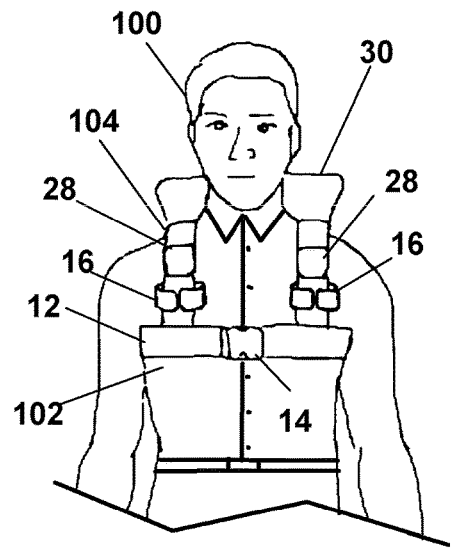
FIG. 7 shows a front view of another particularly preferred mode of the carrier and securement device employing a seating component in the as used position on a user.
Figure 8:
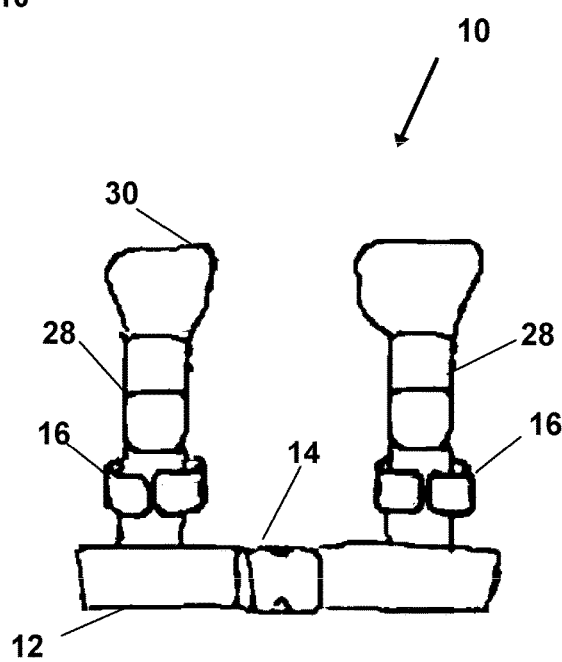
FIG. 8 shows a detailed front view of the device of FIG. 7.
Figure 9:
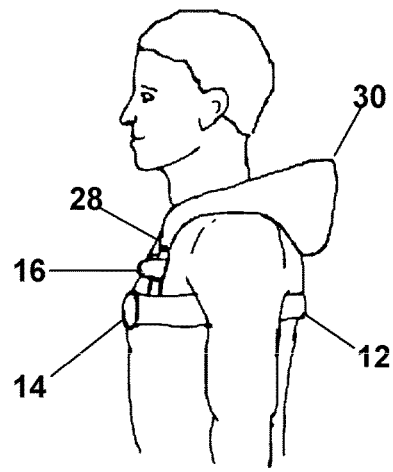
FIG. 9 shows a side view of the device of FIG. 7 in the as used mode.
Figure 10:
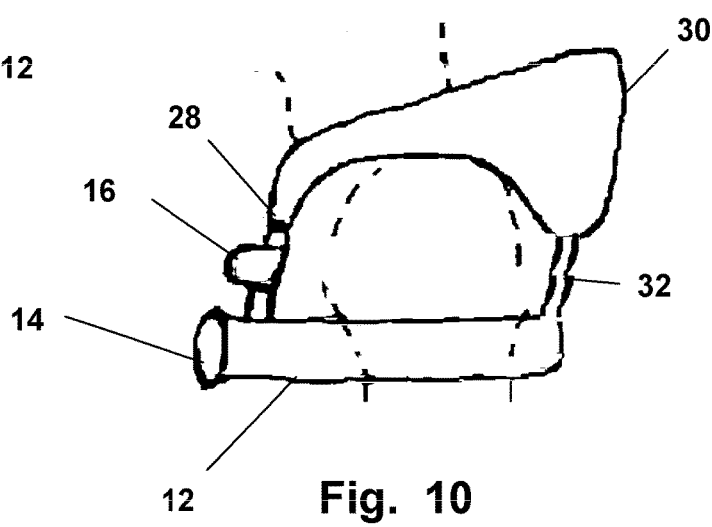
FIG. 10 shows a detailed side view of the device of FIG. 7.

FIG. 6a and FIG. 6b shows views of another particularly preferred mode of the ankle securement members 16 additionally including a flexure portion 26. The flexure portion 26 may be formed as shown to provide a means for biasing the distal ends 18, and 20, toward each other to a retracted or closed position to provide additional securement to maintain the gap 22 smaller than the diameter of the child's leg or ankle.

Additionally providing a flexure means also to allows the gap 22 to be easily increased by moving the two members 16 in opposite directions by an adult when needed. The flexure portion 26 may be provided by an accordion style folding of the ankle member 16 as shown, or other means. For example, the flexure portion 26 can be provide by a portion of flexible fabric, rubber, or the like.

FIG. 7, FIG. 8, FIG. 9, and FIG. 10 shows views of yet another particularly preferred mode of the child carrier and securement device 10 employing the provisions of the previous mode of the device 10 and additionally including a seating component 30. The seat 30 may be formed from a flexible and durable fabric, such that the device 10 can be folded or stored in a relatively small storage volume, however provide a secured seating configuration for a child when in the as used mode. In other modes of the device 10 shown in later figures, the seat 30 may be padded as well as ergonomically contoured as needed. As is shown the seating component 30 is engaged to the chest strap 12 by at least one shoulder strap 28. Further, it is preferred that the ankle members 16 are engaged to the shoulder strap 28 as this configuration conventionally registers with the natural leg position of a child seated atop the users shoulders 104, or in the alternative, pivoting pairs of angle members 16 are employed to allow for angled engagement through the paired leg members 16 when the child's legs approach at an angle. However, other suitable configurations may be employed and are anticipated.

It is optional but preferred that the seat 30 includes a back strap 32 which engages the back of the seat 30 to the back of the chest strap 12. This will substantially increase the securement of the child in the seat 30 by limiting the vertical and horizontal motion of the seat 30 on the users shoulders at is restrained. The back strap 32 may also include a releasable fastener such as hook and loop fabric, or may be unitarily formed with the seat 30 and chest strap 12 by sewing, stitching, or other means.

The device 10 is configured to greatly reduce the stress and strain conventionally imparted on a users neck and back when carrying a child atop their shoulders by transmitting a substantial amount of the stresses to the shoulder straps 28 and chest strap 12. As such an adult can carry a child in such a position for longer and with much more comfort.

Figure 11:
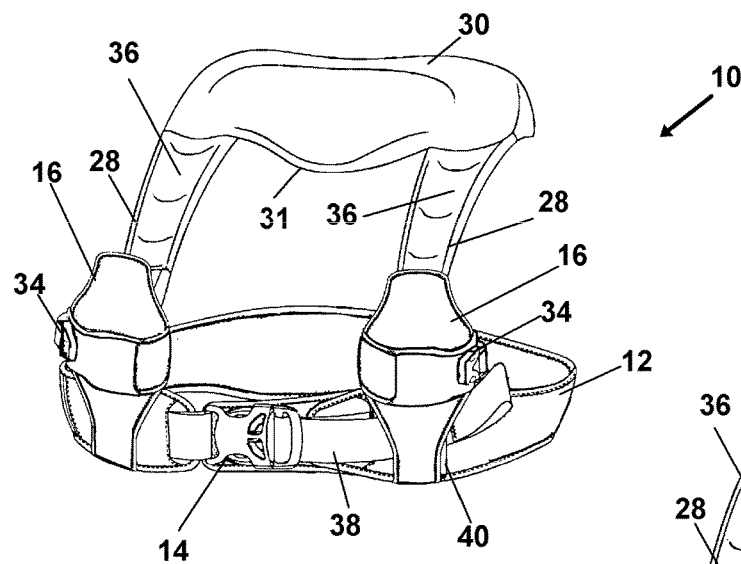
FIG. 11 shows a view of yet another particularly preferred mode of the device having padded straps and ankle securement members, also showing a preferred ergonomic seat and shoulder strap configuration.
Figure 12:
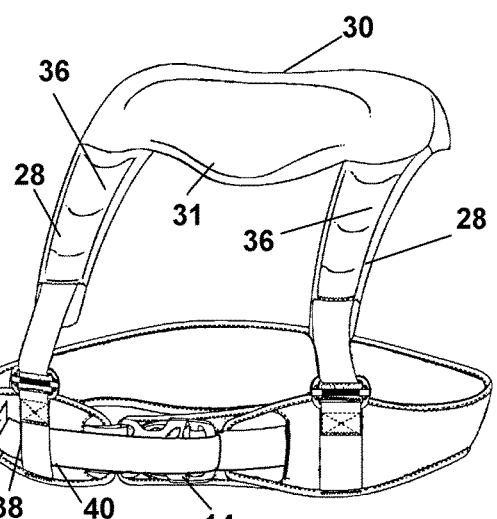
FIG. 12 shows a view of still yet another particularly preferred mode of the device without ankle securement members, and employing means for redundant securement the of the chest strap to the users bust for safety purposes.

Additional securement and comfort may be provided by the modes of the device 10 shown in FIGS. 11 and 12. In FIG. 12, there is shown yet another particularly preferred mode of the device 10 having a seat 30 which is substantially contoured 31 having a lower mid section and a rear portion 31 higher in elevation than the mid section, or otherwise formed to the ergonomics of a sitting child. In this manner the seat 30 may take the form of a saddle or other such configuration. It is noted that those skilled in the art may recognize other contours, shapes, and configuration of the seat 30 to provide comfortable and ergonomic seating, and is anticipated. A rear portion 31 higher than the sunken mid portion, provides a means to prevent the child from falling backwards easily as it supports the lower back and is thus preferred, especially if the ankle members 16 are not employed.

Further, there is shown another preferred mode of the shoulder straps 28 which may be substantially padded or otherwise cushioned to provide added comfort. Additionally, it is clearly shown and preferred that at least one surface of the shoulder straps 28 are substantially concaved 36. This concavity 36 of the shoulder straps provides a means for a registered engagement of a seated child's legs extending over the users chest and inline with the shoulder straps 28. This is especially preferred since the child's legs can comfortably rest on the concave surface 36 without the discomfort of any protruding shoulder strap 28 material, and it provides better support during quick movements of the wearer to prevent a dismount of the rider. The concave surface 36 may be formed by inserting concave planar supports of polymer or plastic material into pockets in the formed strap material which may be seat belt type webbing formed or narrow weave nylon or polyester material.

Still further, yet another preferred mode of the ankle securement members 16 are shown herein formed as releasable straps. The ankle members 16 may be padded, and include a releasable fastener 34 such as a buckle or the like which will provide a means for removable secured engagement of the child's legs or ankles therein. In addition, the ankle members 16 may be permanently or removably engaged to the shoulder 28 and chest straps 12 via sewing or hook and loop fastener respectively, or other suitable means.

The adjustability of the chest strap 12 in the current mode is provided by an adjustable strap 38 which can be lengthened or shortened relative the secured fastener 14 being, for example, a conventional buckle as shown. Added utility is provided in that the distal end of the adjustment strap 38 can be tucked or otherwise secured within a passage 40 formed between the distal end of the shoulder strap 28 and the chest strap 12. The passage 40 can be formed by stitching or otherwise engaging only the terminating end of the shoulder strap 28 to the chest strap 12 and leaving a portion of the shoulder strap 28 disengaged such that the distal end of the adjustment strap 38 can be tucked under.

Figure 13:
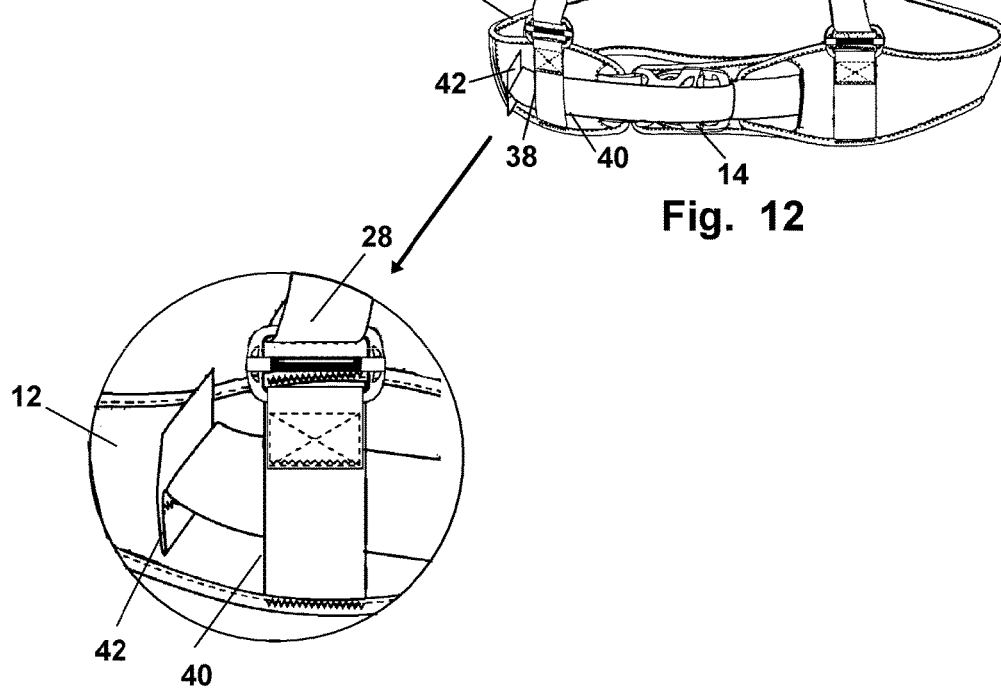
FIG. 13 shows a detail view of the means for redundant safety securement employing MOLLE style strap ends.

FIG. 12 and FIG. 13 show yet another particularly preferred mode of the device 10 wherein means for redundant safety securement of the chest strap 12 are provided. This mode may or may not include ankle members 16, however, in any mode of the device 10 previously it is preferred to include these provisions. As is shown the distal end 42 of the adjustment strap 38 is stitched, sewn, or otherwise formed into a substantially T-shaped cross section, similar to conventional MOLLE style straps. As such, after engaging the securing fastener 14 of the chest strap 12, the distal end 42 of the adjustment strap 38 can be communicated back over the fastener 14 and tucked in an engagement with the passage 40 formed on that side. Therefor, in the event of an accidental disengagement of the fastener 14, the adjustment strap 38 will provide an additional means for maintaining the chest strap 12 in a secured engagement until the user can re-engage the fastener 14.

Figure 14:
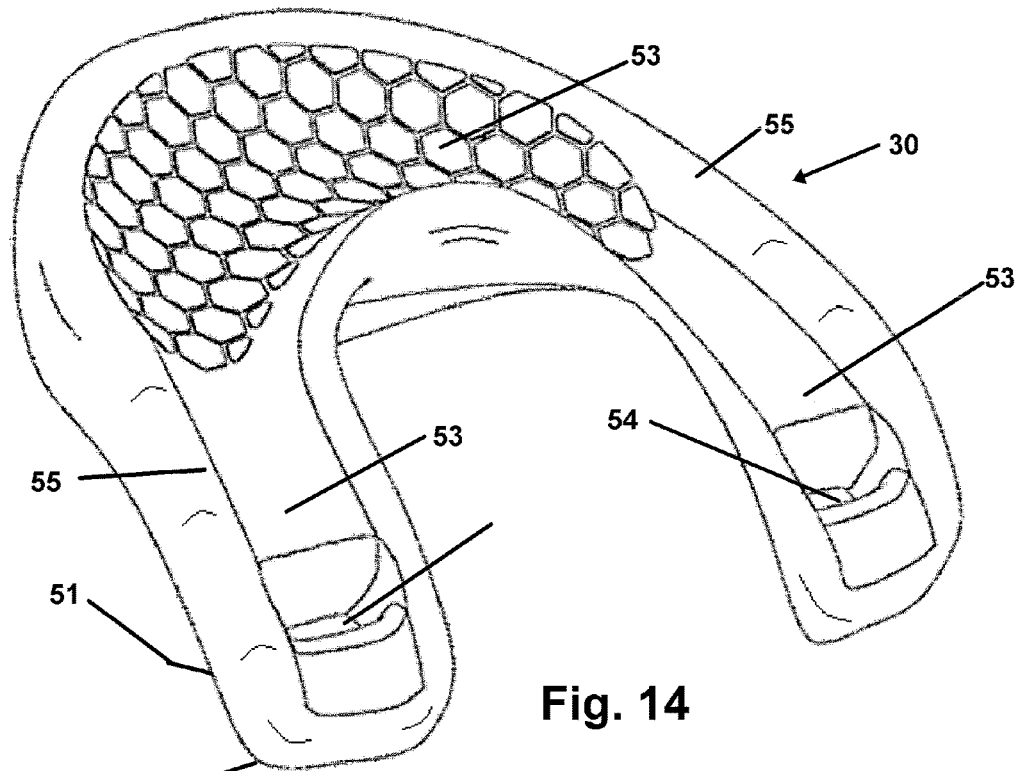
FIG. 14 depicts a particularly preferred mode of the shoulder-positioned pad or pillow interface having leg and posterior engaging recesses, and channels formed for strap engagement.

FIG. 14 depicts a particularly preferred mode of the shoulder-positionable pad or pillow providing a seat 30 which provides an interface between the posterior of the child and the adult or carrying person. As depicted in the preferred mode, the seat 20 has a channel 51 communicating into the lower end of the seat 30 to allow straps 28 (FIG. 10 or 15) to communicate through the channel 51, into and out of the seat 30, on the lower side, opposite the upper side depicted in FIG. 14. The upper side shown, has preferred recesses 53 configured to fit to and accommodate the legs and posterior of the child in the seat 30. The recesses 53 render the seated child more securely positioned on the top of the seat 30, since exterior edges 55 are formed which better hold the child in the recesses 53 and keep the occupant from sliding off the seat 30. The occupant of the seat 30 is thus in a saddled position and secure. This is especially helpful when the user or adult is bending or running or otherwise moving where the child can become dismounted due to the forces of movement.

Figure 15:
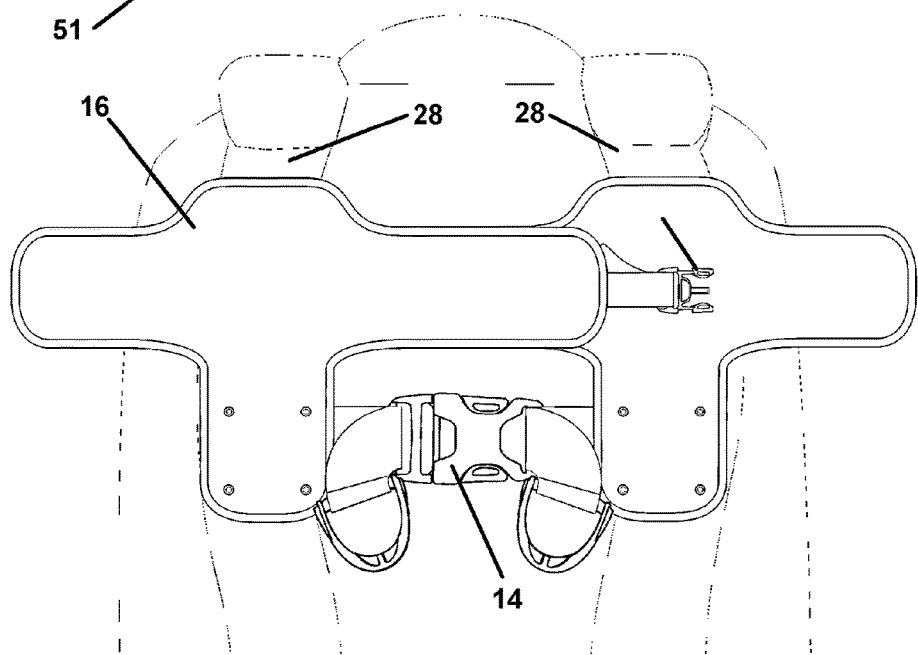
FIG. 15 depicts a mode of the device configured for engagement to a strapped shoulder carrier such as a backpack.
Figure 19:
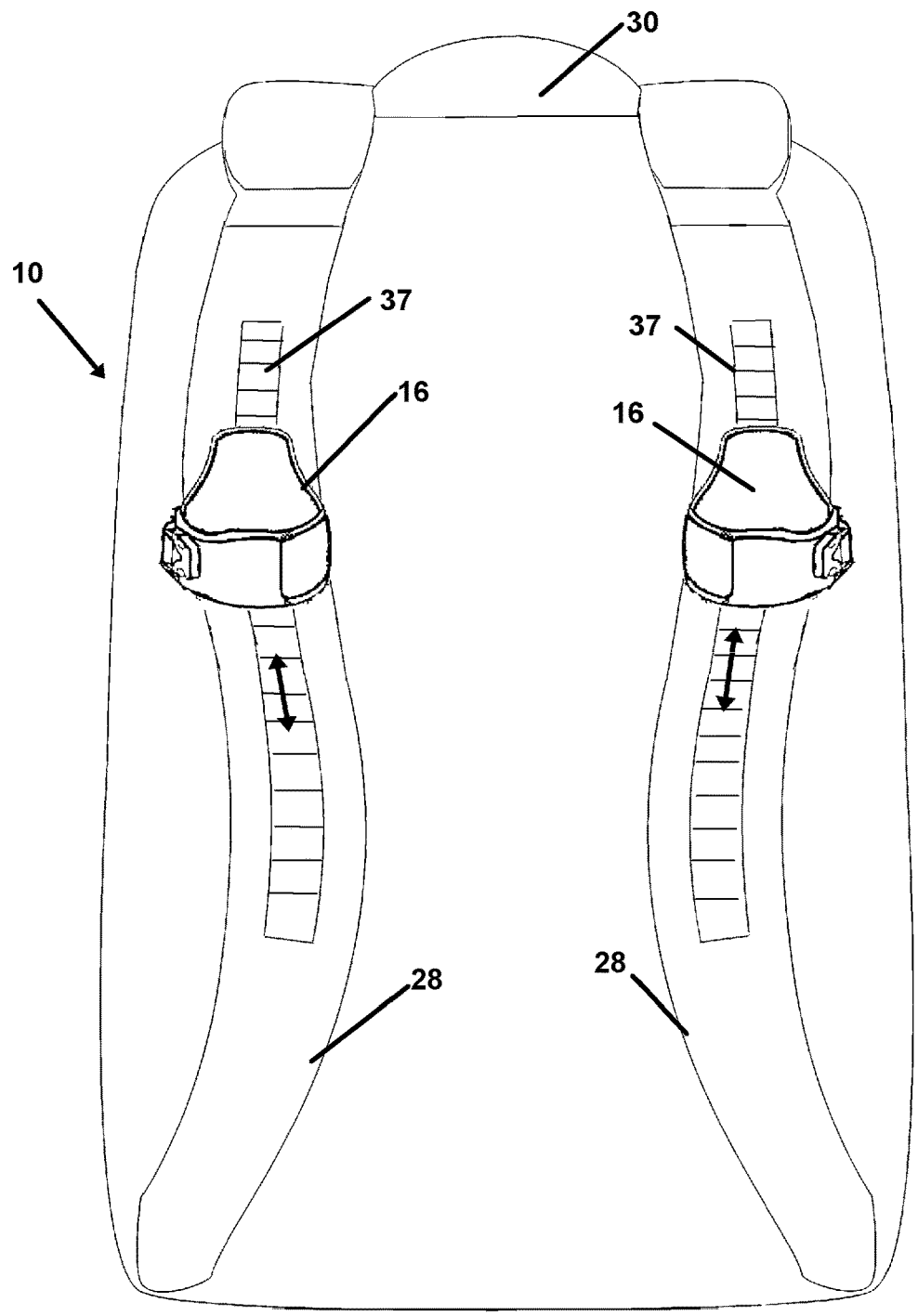
FIG. 19 depicts a mode of the device which is built into a backpack or the like where the leg or ankle restraints are slidably located on the shoulder straps and the pillow or pad would be positioned or part of the top of the backpack.

FIG. 15 depicts a mode of the device 10 configured for removable engagement to the straps 28 of a strapped shoulder carrier such as a backpack 60 (FIG. 19). The ankle members 16 for securing the child's legs are removably engaged with the straps 28 of the existing backpack 60 using means for slidable removable engagement. In the current preferred mode of the device 10 for such strap 28 engagement, 57 clips 43 are engaged to the flexible material forming the ankle members 16 which are slidably engageable upon the straps 28. A centrally located strap 28 is secured with fasteners 14 to impart a bias against the clips 43 in a direction toward each other when engaged on the straps 28 from the outside edge. This inward bias prevents the clips 43 from sliding off the outside edge of the straps 28 thereby holding both ankle members 16 securely and maintaining the straps 28 in a substantially fixed distance from each other concurrently.

Figure 16:
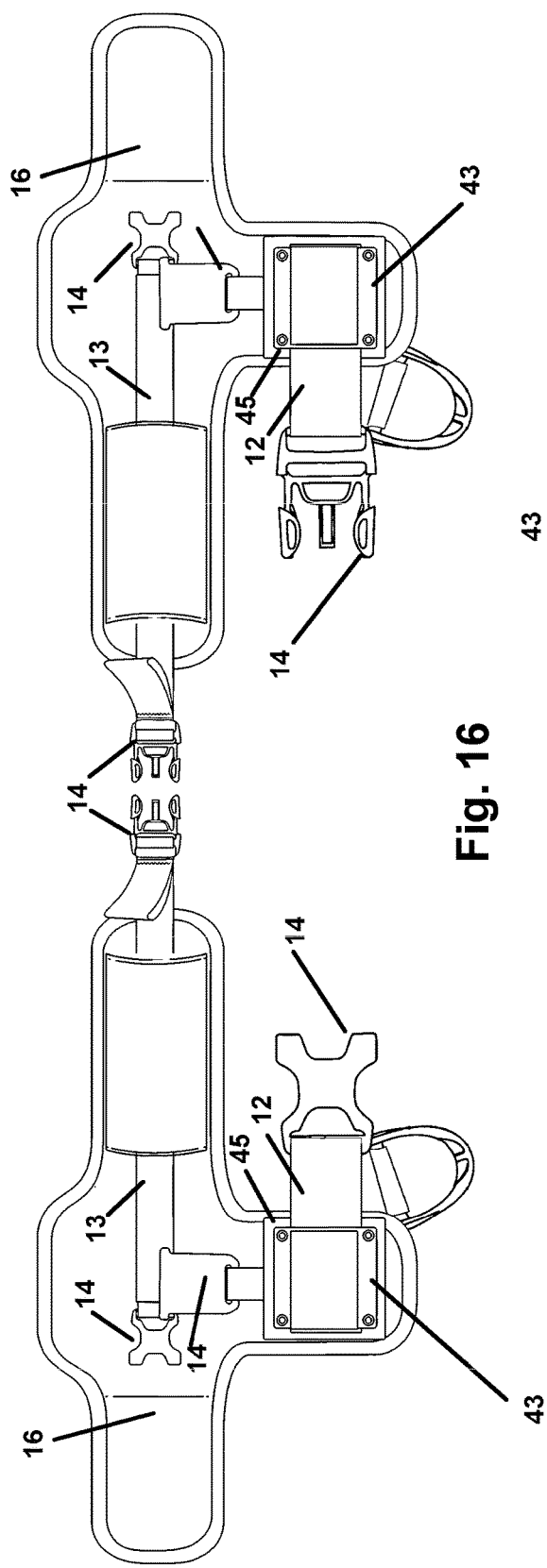
FIG. 16 depicts a rear view of the pair of strap-engageable flexible ankle restraining members of FIG. 15.

FIG. 16 depicts a rear view of the pair of strap-engageable flexible ankle restraining members 16 of FIG. 15. As shown, straps 13 and cooperative fasteners 14 provided a means for encircled engagement of the legs of the child with the body of the ankle restrain 16. The straps 13 may be elastic to provided a biased encircled engagement if desired. Also shown are the rear of the clips 43 engaged to the body of the restraining members 16.

Figure 17:
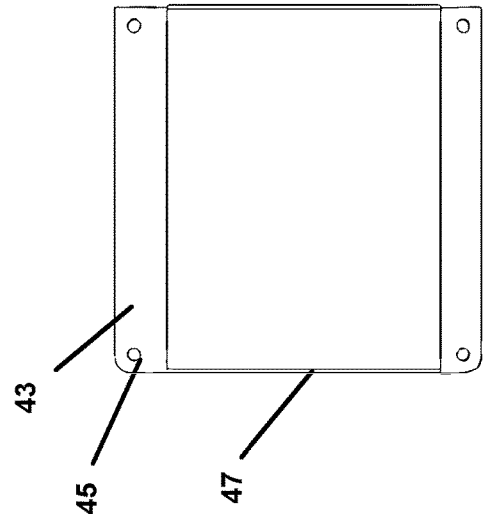
FIG. 17 shows a top plan view of a clip member configured for an engagement with an existing strap of a shoulder-engaged carrying device such as a backpack.
Figure 18:
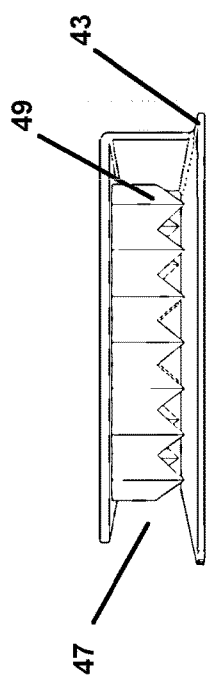
FIG. 18 shows an end view of the device of FIG. 17 and the side opening sized for translation of a strap therein.

FIGS. 17-18 show views of the clip 43 and the attachment points 45 where a rivet or grommet or sewing or other means of attachment to the body of the restraints 16 may be employed. Also shown is the gap 47 allowing insertion of the outside edge of both respective straps 28 into the clips 43. Member configured for an engagement with an existing strap of a shoulder engaged device such as a backpack. Fabric engaging pins 48 are provided inside the gap 47 to form a removable contact with the fabric forming the straps 28.

FIG. 19 depicts a mode of the device 10 which is built into a backpack 60 or other shoulder carrying device with straps 28. In this mode of the device 10, the leg or ankle restraint members 16 providing leg securement, are slidably located using a track 37 on the shoulder straps 28, and the pillow or pad forming a seat 30 can be positioned upon, or be formed as part of the top of the backpack 60. A collar encircling the straps 28 might also be used for a slidably engageable means for engagement of the restraints 16 to the straps 28.

Figure 20:
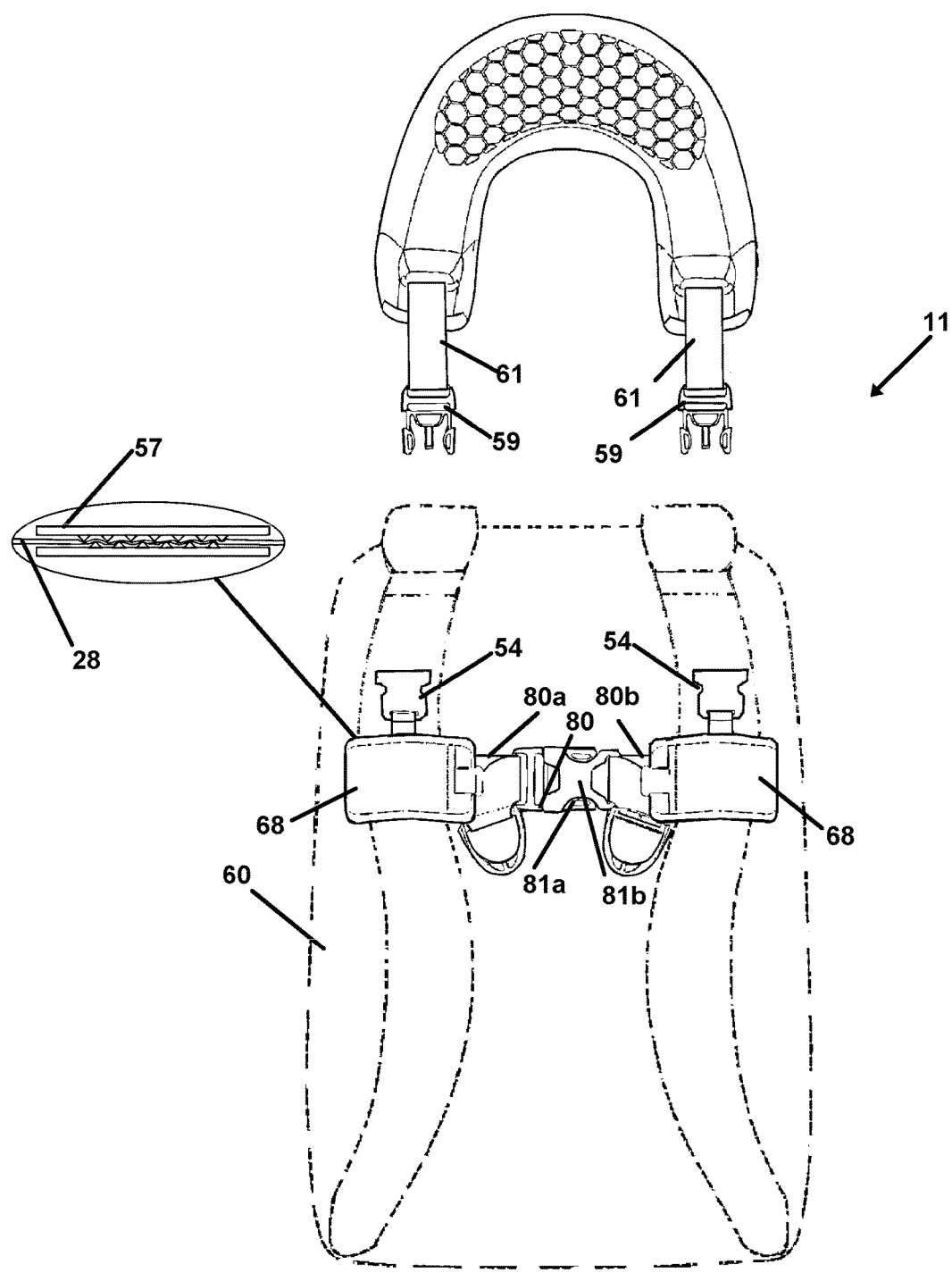
FIG. 20 depicts a mode of the device herein having leg or ankle restraints adapted for fixed positioning on any conventional strap for holding a backpack or the like, and having a shoulder positionable pad or pillow configured to engage both restraints once engaged to a strap.

Shown in FIG. 20 is another mode of the device 11 herein provided in a manner adapted to employ the device 11 which is adapted for engagement and use with an already existing backpack 60. Such will work especially well for user who may have their own or a favored strapped carrier such as a backpack 60 depicted in broken line, but may still wish to employ the device 11 on some occasions.

As shown in FIG. 20, two removably engageable ankle restraints or cuffs 68 are provided by the ankle members 16 which may be engaged around the ankles or legs of a child or rider. The ankle members are shown in FIGS. 21-24 in different views depicting the secure but easily engaged clips 57 which are configured for easy but very secure engagement with the straps 28 of a strapped carrier such as the depicted backpack 60.

Shown in FIG. 20 in the circular blow-up, the preferred clips 57 feature opposing engageable mating clip components 57*a* and 57*b* where each has conical or pyramid shaped projections 75 which are positioned to fall within gaps 77 in between the like projections of the other of the two clip components when held in a compressed or biased engagement by a securing strap 70 having hook and loop fastening material 72 operatively positioned thereon such as shown in FIGS. 23-24.

Figure 21:
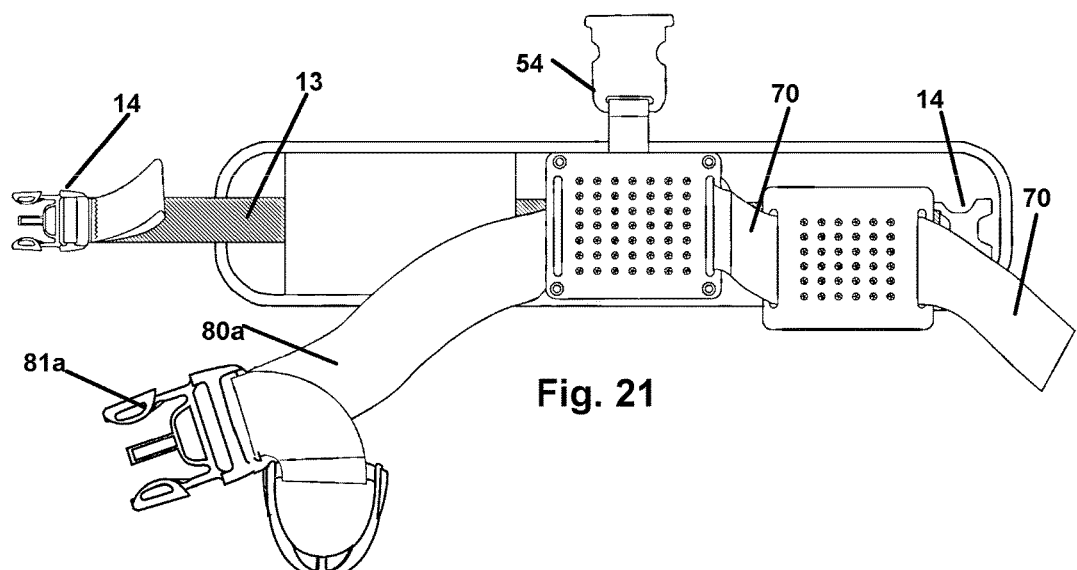
FIG. 21 depicts a rear view of a first strap engaging cuff showing the novel clamp positionable to a fixed engagement with a strap of a backpack or the like through engagement of two mating halves with a strap and also shows connections to engage a second cuff as well as one depending strap from the pad or pillow.

Additionally shown in FIG. 20 and FIGS. 21-21 are mating fasteners 54 extending from an engagement to each of the cuffs formed by a strap member 16 once encircled around a rider's ankle or legs. The mating fastener 54 is configured to engage fastener 59 engaged upon the distal end of a seat strap 61 extending from an engagement with one side of the seat 30. When both mating fasteners 54 are removably engaged with both fasteners 59, the seat is tethered to each of the two cuffs, which are in a removable but fixed engagement to a strap 28 has explained below.

Figure 22:
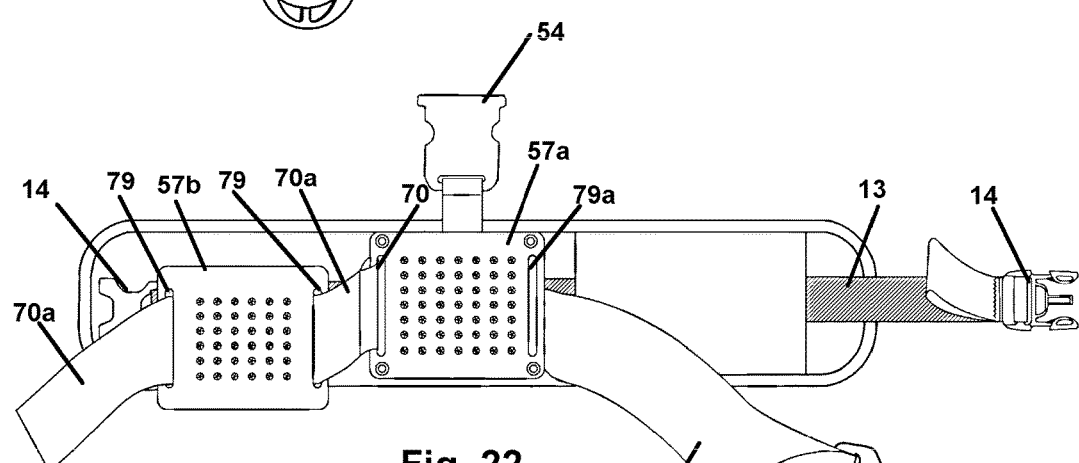
FIG. 22 shows a rear view of the second strap engaging cuff which is engageable to the first cuff using as well as with a second strap depending from the pad or pillow.

As shown in FIGS. 21-22, the clip 57 which is positioned to the rear of the ankle members 16 of FIG. 20, when formed of first clip component 57*a* and second clip component 57*b*, has been found through experimentation to yield an especially secure engagement to a strap 28 of a backpack 60 or strapped container. This is most important since if a child's legs are secured by the ankle members 16 at a desirable position, any sliding upward can allow a secured child to fall rearward further than is desirable.

Figure 22A:
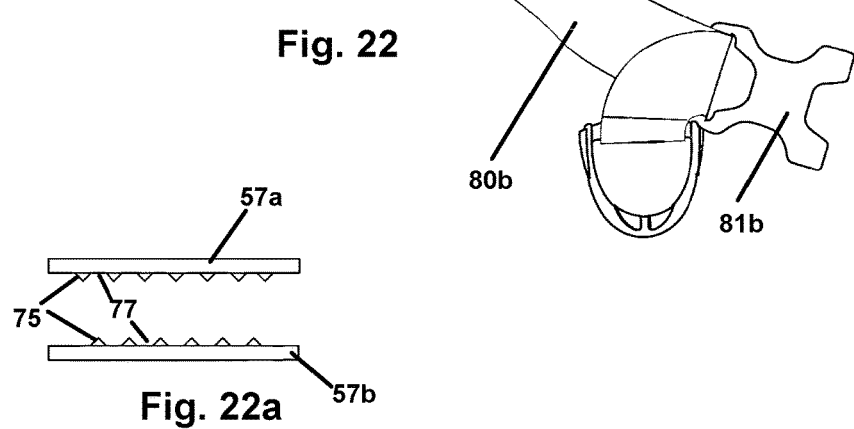
FIG. 22a depicts a side view of the two mating clip components which are particularly preferred where the projections of one component are in positions to fall within caps between like projections of the other mating clip component.

As shown in FIGS. 21-22*a*, it was found that by positioning the projections 75 in registered patterns on both the first mating clip component 57*a* and second mating clip component 57*b*, where the projections 75 on each respective clip component will fall within a gap 77 on the other of the respective clip components of 57*a* and 57*b*, that a much more secure engagement of the attached ankle member 16 is achieved to the strap 28. Sliding on the strap 28 using the depicted and preferred clips 57 is eliminated when the clip components 57*a* and 57*b* are held in a biased or compressed engagement on both sides of the strap 28 by the securing strap 70.

As can be seen best in FIGS. 21-22, a first end of the securement strap 70 is to a slot 79 formed in one end of the first clip component 57*a*. The securement strap 70 is slidingly engaged through two slots upon opposite sides of the second clip component 57*b* leaving a distal end portion 70*a* of the securement strap 70 extending from one slot 79 of the second clip component 57*b*.

In use, to removably engage the clip 57 to a strap 28 of a strapped carrier such as a backpack 60, the distal end portion 70*a* of the securement strap 70 is pulled through an open slot 79*a* of the first clip component 57*a*, and the two clip components 57*a* and 57*b* are placed in a biased or compressed engagement on both sides of a strap 28. The distal end 70*a* of the securement strap 70, which one portion of hook and loop fastener 72 thereon as shown in FIGS. 23-24, is operatively engaged with mating portion of hook and loop fabric 72*a* engaged to the securement strap 70 at a position adjacent to the rear side of the second clip component 57*b*.

This mode of engagement of the clips 57 to straps 28 has proven during experimentation to be easy to accomplish and especially secure since the securement strap 70 pulled through the slot 79*a* and then secured by the hook and loop fabric, allows the user to pull on the securement strap 70 which will compress and bias the projections 75 on both halves of the clip 57 into the strap 28 and push the strap 28 into a serpentine engagement between the projections 75 and gaps 77 of both of the two clip portions 57*a* and 57*b* because the projections 75 on both are in positions registered with gaps 77 on the other of the two clip portions 57*a* and 57*b*. The achieved serpentine path of the strap 27 between both of the compressed clip portions 57*a* and 57*b* and in the serpentine path over respective projections 75 and into respective caps 77, has shown to prevent any sliding of the clip 57 and movement of the attached ankle members 16, such that once locked into removable engagement with a strap 28 by the hook and loop fabric on the securement strap 70, the clips 57 stay engaged and do not move for the duration of their removable engagement to a strap 28.

Additionally shown in FIG. 20 is a sternum strap 80 formed of two strap portions 80*a* and 80*b* which are engaged to each other using mating fasteners 81*a* and 81*b*. The sternum strap 80 is also particularly preferred in all modes of the device 11 because once the two halves are secure by the fastener 80, it maintains the straps 28 of the backpack 60 at a fixed maximum distance from each other and prevents the straps 28 from slipping over the shoulder of the user. This is most important since if one of the straps 28 slips off the user's shoulder, the device 10 can dismount concurrently with the backpack 60 and a child occupying the seat 30 could be injured.

FIG. 21 depicts a rear view of a first strap engaging cuff showing the novel clamp positionable to a fixed engagement with a strap of a backpack or the like through engagement of two mating halves with a strap and also shows connections to engage a second cuff as well as one depending strap from the pad or pillow.

FIG. 22 shows a rear view of the second strap engaging cuff formed by an ankle member 16 which forms a cuff when the strap 13 running along the long axis of the ankle member 16 has both ends engaged by cooperatively engaging fasteners 14 such as the pin and socket type clips shown. As noted the formed second cuff by the encircled ankle member 16 is engageable to the second of the two cuffs by the sternum strap 80, and is engageable with one of the two securing straps 61 attached to the seat 30 to hold the seat 30 in position about the rear of the user's neck.

As noted FIG. 22a shows a side view of the two mating clip portions 57a and 57b, which are particularly preferred where the projections 75 of one are in positions to fall within gaps 77 between like projections 75 of the other mating clip component from the two. This mated engagement restrains the strap 28 between the two clip portions in the serpentine engagement shown in the circular blow up of FIG. 20.

FIGS. 23-24 each show a front view of one cuff 68 as depicted in FIG. 20, each of which is formed by the ankle member 16, when wrapped around the leg or ankle of a child, and held by the strap 13 and two engaged mating engaging fasteners 14. As noted earlier, the strap 13 may be formed of elastic material to achieve a biased encirclement of the formed cuff 68 around the leg of a child. Also show is the securement strap 70 extending from its engagement to one of the clip portions, and showing the hook and loop fabric sections 72a and 72, engaged upon one side surface of the securement strap 70 in positions to engage with each other once the two clip portions 57a and 57b have formed the clip 57 which is compressed upon a strap 28.

It is noted and anticipated that although the device is shown in its most simple form, various components and aspects of the device may be differently shaped or slightly modified when forming the invention herein. As such, those skilled in the art will appreciate the descriptions and depictions set forth in this disclosure or merely meant to portray examples of preferred modes within the overall scope and intent of the invention, and are not to be considered limiting in any manner.

This invention has other applications, potentially, and one skilled in the art could discover these. The explication of the features of this invention does not limit the claims of this application; other applications developed by those skilled in the art will be included in this invention.

While all of the fundamental characteristics and features of the invention have been shown and described herein, with reference to particular embodiments thereof, a latitude of modification, various changes and substitutions are intended in the foregoing disclosure and it will be apparent that in some instances, some features of the invention may be employed without a corresponding use of other features without departing from the scope of the invention as set forth. It should also be understood that various substitutions, modifications, and variations may be made by those skilled in the art without departing from the spirit or scope of the invention. Consequently, all such modifications and variations and substitutions are included within the scope of the invention as defined by the following claims.

What is claimed is:

1. A child carrier apparatus adapted for removable engagement to a carrier having shoulder straps and providing secure seating for a child, atop shoulders of a wearer, comprising;

a first cuff, said first cuff having formed of a first flexible cuff member sized for an encircled engagement around one leg of said child;

a second cuff, said second cuff formed of a second flexible cuff member sized for an encircled engagement around one leg of said child;

a first clip, said first clip attached to said first cuff and removably engageable with a first shoulder strap of said carrier;

a second clip, said second clip attached to said second cuff and removably engageable with a second shoulder strap of said carrier;

a seat having a first side surface opposite a second side surface;

said first side surface adapted for positioning upon the shoulders of said wearer;

a first seat strap extending between a first end engaged with said seat to a second end in an engagement with said first cuff;

a second seat strap extending between a first end engaged with said seat to a second end in a second engagement with said second cuff;

said first clip and said second clip each formed of a respective first clip component and a second clip component;

each said first clip component having a first side and a second side;

each said second clip component having a first side and a second side;

said first side of each said first clip component having a plurality of projections extending therefrom having gaps therebetween;

said first side of each said second clip component having a plurality of projections extending therefrom having gaps therebetween;

a strap engageable between each said first clip component and said second clip component to hold said first side of each respective said first clip component in an engaged position facing said first side of a respective said second clip component;

said projections extending from said first side of each said first clip component positioned within said gaps formed upon said first side of each said second clip component with said first clip component in said engaged position;

each of said first shoulder strap and said second shoulder strap following a serpentine pathway between a respective said first clip component and said second clip component; and whereby said first cuff and said second cuff operatively engaged with respective said legs of said child sitting in said seat prevent said legs from rising above said shoulders of said wearer and concurrently prevent said child from falling from said seat.

2. The child carrier apparatus of claim 1 additionally comprising:

a sternum strap extending a distance between a first end thereof engaged with said first cuff and a second end thereof engaged with said second cuff; and said sternum strap defining a maximum distance of separation between said first shoulder strap and said second shoulder strap.

3. The child carrier apparatus of claim 1 additionally comprising:

said engagement of said first seat strap with said first cuff being a removable engagement formed by an engagement between a first fastener engaged to said seat strap and a mating first fastener engaged to said first cuff; and said engagement of said second seat strap with said second cuff being a removable engagement formed by an engagement between a second fastener engaged to said seat strap and a mating second fastener engaged to said second cuff.

4. The child carrier apparatus of claim 2 additionally comprising:

said engagement of said first seat strap with said first cuff being a removable engagement formed by an engagement between a first fastener engaged to said seat strap and a mating first fastener engaged to said first cuff; and said engagement of said second seat strap with said second cuff being a removable engagement formed by an engagement between a second fastener engaged to said seat strap and a mating second fastener engaged to said second cuff.

5. The child carrier apparatus of claim 2 additionally comprising:

a first portion of said sternum strap extending between said first end thereof engaged with said first cuff and a first sternum fastener;

a second portion of said sternum strap extending from said second end thereof engaged with said second cuff and a first mating sternum fastener; and said first sternum fastener removably engageable to said first mating sternum fastener.

6. The child carrier apparatus of claim 4 additionally comprising:

a first portion of said sternum strap extending between said first end thereof engaged with said first cuff and a first sternum fastener;

a second portion of said sternum strap extending from said second end thereof engaged with said second cuff and a first mating sternum fastener; and said first sternum fastener removably engageable to said first mating sternum fastener.

7. A child carrier apparatus adapted for removable engagement to a carrier having shoulder straps and providing secure seating for a child, atop shoulders of a wearer, comprising;

a first cuff, said first cuff having formed of a first flexible cuff member sized for an encircled engagement around one leg of said child;

a second cuff, said second cuff formed of a second flexible cuff member sized for an encircled engagement around one leg of said child;

a first clip, said first clip engaged upon said first cuff;

said first clip having a first clip component and a second clip component;

said first clip removably engageable to a first biased compressive engagement of a first shoulder strap of said carrier when positioned in-between said first clip component and said second clip component;

a second clip, said second clip engaged upon said second cuff;

said second clip having a first clip component and a second clip component;

said second clip removably engageable to a second biased compressive engagement of a second shoulder strap of said carrier when positioned in-between said first clip component of said second clip and said second clip component of said second clip;

said first biased compressive engagement of said first clip to said first shoulder strap defining a removable engagement of said first cuff thereto;

said second biased compressive engagement of said second clip to said second shoulder strap defining a removable engagement of said second cuff thereto;

a seat having a first side surface opposite a second side surface;

said first side surface adapted for positioning upon the shoulders of said wearer;

a first seat strap extending between a first end engaged with said seat to a second end in an engagement with said first cuff;

a second seat strap extending between a first end engaged with said seat to a second end in a second engagement with said second cuff;

and whereby said first cuff and said second cuff operatively engaged with respective said legs of said child sitting in said seat, and in respective said removable engagements to said first and second shoulder strap, prevent said legs of said child from rising above said shoulders of said wearer, and concurrently prevent said child from falling from said seat.

8. The child carrier apparatus of claim 7 additionally comprising:

each respective said first clip component of said first claim and said second clip, having a first side and a second side;

each respective said second clip component of said first clip and said second clip, having a first side and a second side;

said first side of each said first clip component having a plurality of projections extending therefrom having gaps therebetween;

said first side of each said second clip component having a plurality of projections extending therefrom having gaps therebetween;

said projections extending from said first side of each said first clip component positioned within said gaps formed upon said first side of each said second clip component with said first clip component in said engaged position; and whereby said first cuff and said second cuff operatively engaged with respective said legs of said child sitting in said seat, with a respective said biased compressive engagement of said first clip and said second clip upon said first shoulder strap and second shoulder strap, prevent said legs from rising above said shoulders of said wearer and concurrently prevent said child from falling from said seat.

\* \* \* \* \*